United States Patent [19]

Moss

[11] 4,266,545
[45] May 12, 1981

[54] PORTABLE SUCTION DEVICE FOR COLLECTING FLUIDS FROM A CLOSED WOUND

[76] Inventor: James P. Moss, 250 E. Liberty St., Louisville, Ky. 40202

[21] Appl. No.: 27,835

[22] Filed: Apr. 6, 1979

[51] Int. Cl.³ .............................................. A61M 1/00
[52] U.S. Cl. .................................. 128/278; 417/274; 128/234; 128/767
[58] Field of Search .............. 417/234, 274, 383, 389, 417/394, 395; 128/276, 278, 765, 766, 767, 205.18, 763, 234, 240, 218 PA

[56] References Cited

U.S. PATENT DOCUMENTS

| 3,032,037 | 5/1962 | Huber | 128/276 |
|---|---|---|---|
| 3,169,529 | 2/1965 | Koenig | 128/207.14 |
| 3,469,578 | 9/1969 | Bierman | 128/214 F |
| 3,527,215 | 9/1970 | De Witt | 128/272 |
| 3,543,753 | 12/1970 | Weinstein | 128/214 F |
| 3,785,367 | 1/1974 | Fortin et al. | 128/763 |
| 3,809,086 | 5/1974 | Schachet | 128/278 |
| 3,939,830 | 2/1976 | da Costa | 128/278 |
| 3,951,146 | 4/1976 | Arias | 128/218 PA |
| 4,112,949 | 9/1978 | Rosenthal et al. | 128/278 |

Primary Examiner—Robert W. Michell
Assistant Examiner—J. L. Kruter
Attorney, Agent, or Firm—Larson, Taylor and Hinds

[57] ABSTRACT

A portable closed wound suction device is provided which is adapted to be worn on the body following outpatient and other limited surgical procedures. Specifically, the device provides a rigid container which is adapted to be strapped to the body of a patient with a tubular connection to a wound for collecting fluids from the wound. The container is provided with a wall which may be moved from an inactive position to a locked outer position so as to create suction within the device. The rigid container cannot be tampered with by the patient.

5 Claims, 8 Drawing Figures

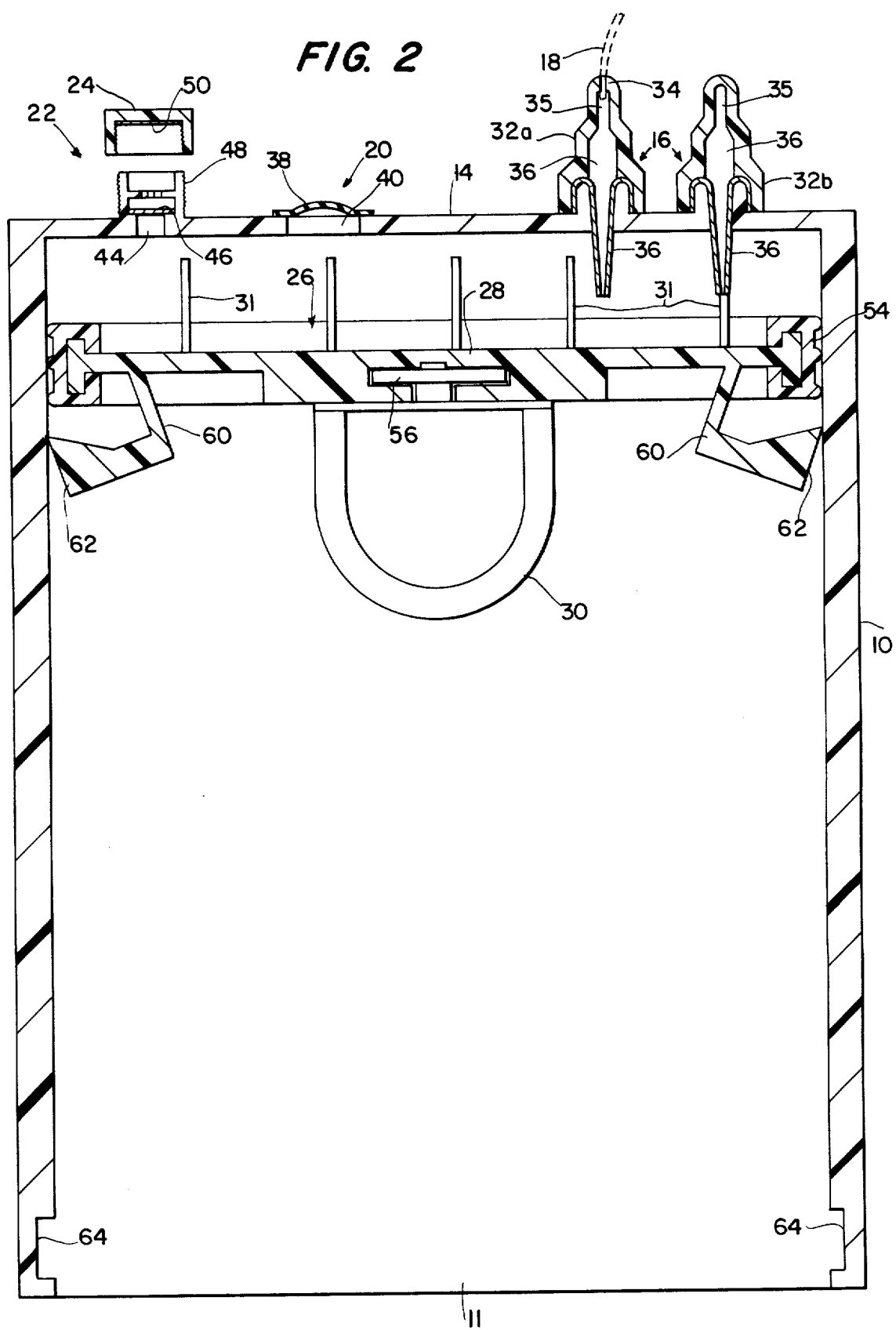

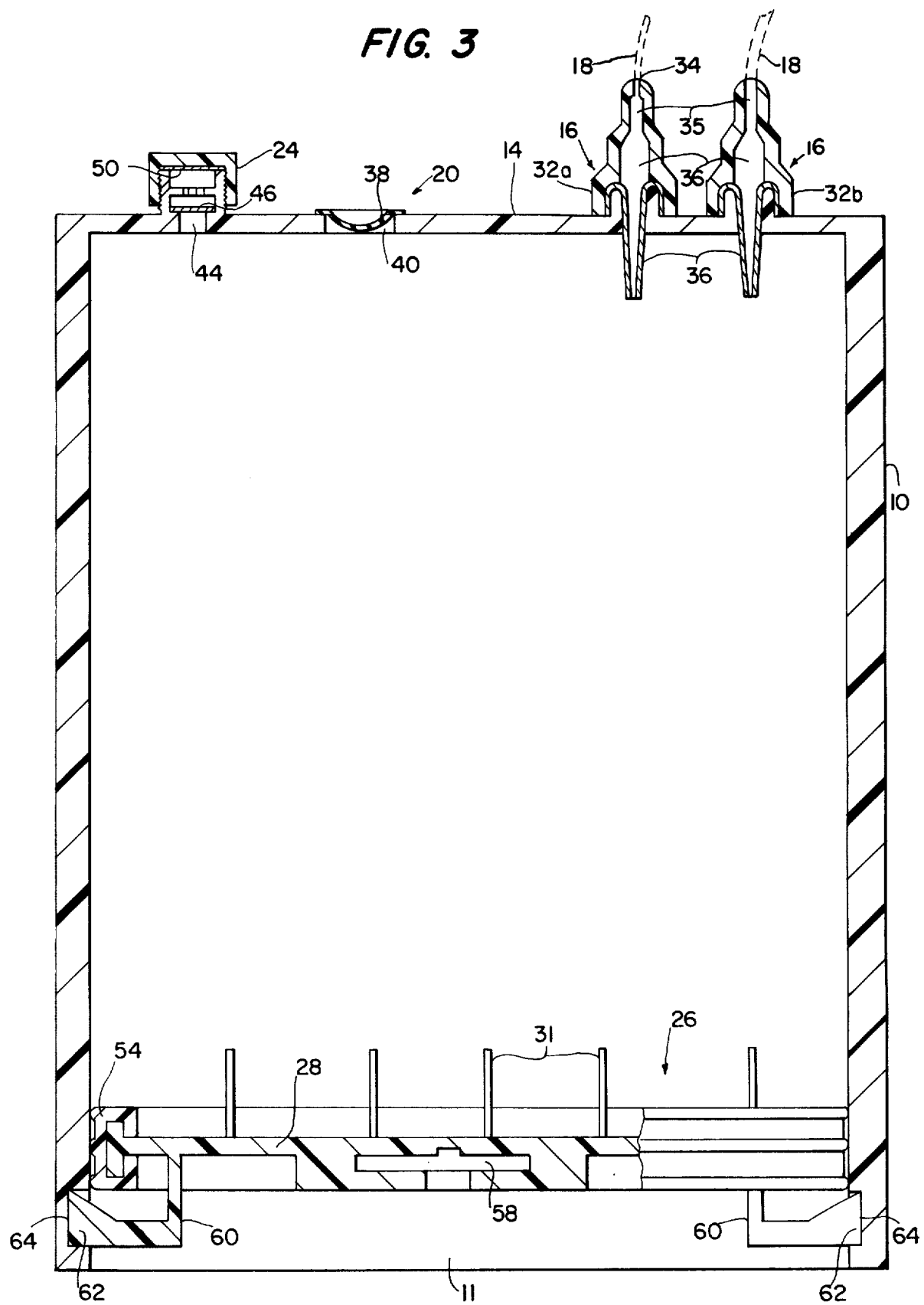

PORTABLE SUCTION DEVICE FOR COLLECTING FLUIDS FROM A CLOSED WOUND

BACKGROUND OF THE INVENTION

The invention relates to a portable closed wound suction device and more particularly, to such a device which may be worn by persons following outpatient surgery and which provides suction to remove fluids from a closed wound in a rigid container having no movable parts which could be tampered with by the patient.

Due to the large increase in recent years in outpatient surgery, there has developed a substantial need for portable collection chambers which may be used with a surgical drain to permit the efflux of blood, serum and body secretions from the operative site to the exterior of the patient. Heretofore, such collection chambers could not be used effectively for outpatient care for the reason that such devices were too bulky to be portable or such devices incorporated movable parts, valves or the like which could be tampered with by the patient so as to render the device inoperative or even to cause body fluids secreted from the wound to be forced back into the body. Thus, there exists a need for a truly portable closed wound suction device which is constructed in such a way that the proper operation of the device cannot be interfered with in any way by the patient.

Typically, prior art devices which are designed for portable closed wound suction are shown in U.S. Pat. Nos. 3,115,138 and 3,376,868. Such devices provide a movable wall or container formed as a bellows which are adapted to be compressed to create a suction therein as the device returns to its original configuration. However, if such devices are accidently compressed by the patient when partially filled, the potentially contaminated body fluids which have been drawn from the wound site will be forced back into the wound area. Other devices such as shown, for example, in U.S. Pat. Nos. 3,900,029 or 3,774,811 are too bulky to be considered adapted to be worn by a patient as a portable unit in the home environment after outpatient surgery.

Numerous attempts have been made in the prior art to provide a reliable suction collection chamber which could be activated by the surgeon following surgery and carried by the patient in the hospital while the wound is healing, but such prior art devices have not met all of the essential criteria set forth hereinbefore, that is, providing a readily portable unit which is formed as a rigid container with no valves, bulbs or movable parts which can be tampered with by the patient.

SUMMARY OF THE INVENTION

The present invention provides a closed wound suction device formed as a container with rigid top and side walls. The bottom wall is movably mounted in sealing engagement with the interior of the container so that it can be moved from a first inoperative position adjacent the top wall of the unit to an operative locked position in substantial spaced relation to the top wall, in which position suction is created within the unit. The container is provided with tube connections by which tubes can be connected with the wound site in a conventional manner. The device is shaped so that it may be readily strapped to the body of the patient adjacent the wound site and the rigid wall construction, including the locked in place bottom wall, does not permit the patient to alter in any way the operation of the device.

There may be provided a diaphragm in the top wall of the collection container to permit taking a sample of the fluid within the container or for removing the fluids within the container for continued use by the patient. Furthermore, there may be provided a suction indicator which serves to indicate the degree of suction existing within the container. The handle or means by which the bottom wall is drawn down to its suction creating position may be removed after the bottom wall is locked in its operative position.

Thus, according to the present invention there is provided a rigid container with substantially non-compressible walls which is readily adaptable to be strapped to the body of a patient and which, when in the operative condition, has no movable parts, valves or bulbs which would permit the patient to alter the correct operative conditions of the unit.

An object of the present invention is to provide a portable closed wound suction device which is particularly well suited for outpatient care.

Another object of the present invention is to provide a rigid wall collection chamber for closed wound suction which is adapted to be strapped to the patient's body which is not subject to being tampered with by the patient.

Other objects and many of the attendant advantages will become more readily apparent upon consideration of the following detailed drawings.

BRIEF DESCRIPTION OF THE DRAWINGS

FIG. 2 is a cross-sectional view of a similar embodiment of the present invention depicted in FIG. 1 with the movable bottom wall in a retracted position.

FIG. 3 is a cross-sectional view of the embodiment of the present invention depicted in FIG. 2 with the movable bottom wall locked in an extended position.

DETAILED DESCRIPTION OF THE PREFERRED EMBODIMENTS

Figure 1:
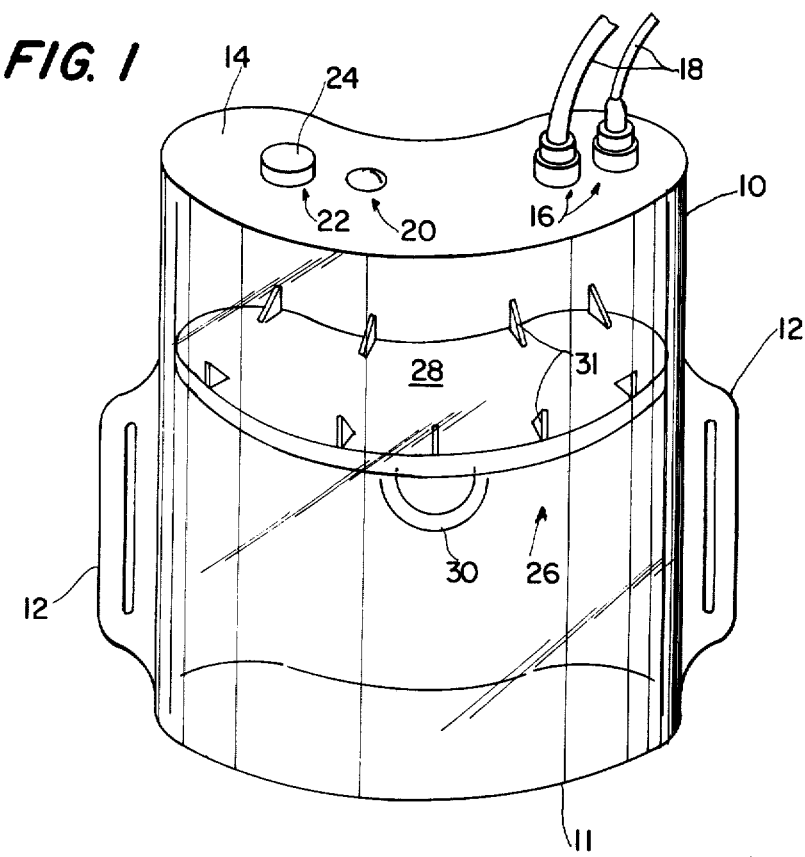
FIG. 1 is a perspective view of one embodiment of the present invention comprising a collection container with a movable bottom wall.

With reference now to the drawings in which like numerals represent like elements throughout the several views, a presently preferred embodiment of the present invention is depicted in FIG. 1 and comprises a rigid container 10 with an open end 11. In order to view the amount of fluid collected in rigid container 10, rigid container 10 is preferably made of a transparent plastic. Rigid container 10 is bow-shaped so that it can be comfortably worn on the body of the user by means of a belt or the like which passes through flanges 12 located on the sides of rigid container 10. Located on top wall 14 of rigid container 10 is port means 16. Port means 16 has drainage tubes 18 attached thereto. Also located on top wall 14 is a suction indicating means 20 and an aspiration port means 22 covered by a cap 24.

Rigid container 10 has a closure means 26 which consists of a movable rigid wall 28 with a pull tab 30. A plurality of spacers 31 placed near the edges of rigid wall 28 prevent rigid wall 28 from pressing against top wall 14.

Referring now also to FIGS. 2 and 3, an embodiment of the present invention, similar to the one depicted in FIG. 1, is shown. This embodiment has a pair of port means 16 which can receive different sizes of drainage tubes 18. Upstanding rubber nipple 32 is attached to the top wall 14 of rigid container 10. Rubber nipple 32a can receive a very small drainage tube 18 in orifice 34. If a slightly larger drainage tube 18 is desired, orifice 14 can be easily cut off of rubber nipple 32a so that orifice 35 receives the slightly larger drainage tube 18. Likewise, orifice 35 can be removed so that orifice 36 can accomodate a still larger drainage tube 18. Rubber nipple 32b is initially closed at the top, but rubber nipple 32b can similarly be trimmed to receive different sized catheters. Extending below each rubber nipple 32 is a one way valve 36 formed of resilient fingers normally biased together but which open to permit fluid flow into rigid container 10.

Suction indicating means 20 is used to determine when a negative pressure exists inside of rigid container 10. A small latex disc 38 is attached over opening 40 to form an airtight seal. When a negative pressure does exist inside of rigid container 10, latex disc 38, which normally protrudes slightly outwardly of rigid container 10 as shown in FIG. 2, is pulled slightly toward the inside of rigid container 10 as shown in FIG. 3.

Aspiration port means 22 is used to withdraw a sample of the liquid which is collected in rigid container 10. Aspiration port 44 in top wall 14 is covered by a puncturable flap 46 made of rubber or the like. Surrounding flap 46 is upstanding wall 48 having exterior screw threads. Cap 24 with mating screw threads and a gasket 50 is normally screwed down on upstanding wall 48 to create a fluid-tight seal. When a fluid sample is desired, cap 24 is removed and a syringe is inserted into rigid container 10 through flap 46 and aspiration port 44. Flap 46, which may leak slightly due to previous punctures, acts to preserve the negative pressure inside of rigid container 10 while cap 24 is temporarily removed.

Closure means 26 is shown in FIG. 2 in its retracted inoperative position, while in FIG. 3 closure means 26 is shown in its extended operative position. A rigid wall 28 with an annular gasket 54 around its periphery forms a closure means 26. Rigid wall 28 is also bow shaped so that it mates with the walls of rigid container 10 to form an airtight seal. A plurality of upstanding spacers 31 are mounted on rigid wall 28 to keep rigid wall 28 in proper alignment as it is moved. Spacers 31 assure that a small air pocket is maintained between rigid wall 28 and top wall 14 and prevents rigid wall 28 from engaging and damaging check valves 36.

In order to draw rigid wall 28 from its retracted position to its extended position, a detachable handle 30 is provided. Detachable handle 30 is attached to rigid wall 28 by means of a key 56 on detachable handle 30 which engages a mating keyway 58 in rigid wall 28. Detachable handle 30 is attached to rigid wall 28 by inserting key 56 into keyway 58 and then turning handle 30 counterclockwise approximately 90°. Handle 30 is easily detached in a like manner by turning handle 30 in a clockwise direction.

Depending from rigid wall 28 are two arms 60 with attached shoulder portions 62. Each arm forms a resilient element which urges shoulder portion 62 outwards. On the side walls of rigid container 10 near open end 11 are recesses 64 which mate with shoulder portions 62. As rigid wall 28 is drawn towards open end 11 by handle 30, shoulder portions 62 are resiliently urged outward and engage recesses 64. This locks rigid wall 28 in place, preventing rigid wall 28 from moving inward or outward.

In operation, the portable closed wound suction device functions in the following manner. First, drainage tube 18 with a suitable catheter on its distal end is inserted into the closed wound which needs to be drained. The proximal end of drainage tube 18 is then inserted in rubber nipple 32 after rubber nipple 32 has been trimmed (if necessary) to the proper sized orifice 34, 35 or 36. A second drainage tube can also be used in a similar manner with the second rubber nipple 32. Normally with two nipples 32 one is manufactured open and the other closed so that one drain is always inserted in the open inlet and, if a second drain is desired, the tip of the second inlet is cut off by the surgeon and the drain inserted. Then, with cap 24 in place over aspiration port 44, the wound suction device is activated when pull tab 30 moves rigid wall 28 from its retracted inoperative position as shown in FIG. 2 to its extended operative position as shown in FIG. 3. When rigid wall 28 reaches open end 11 of rigid container 10, shoulder portions 62 which are resiliently urged outward by arms 60 lock into recesses 64 and hold rigid wall 28 firmly in place. As rigid wall 28 is drawn downward, annular gasket 54 forms a fluid tight seal against the walls of rigid container 10 so that a negative pressure is created and maintained inside of rigid container 10. This negative pressure causes any fluids located around the catheter to be drawn or sucked through drainage tube 18 and check valve 36 into the interior of rigid container 10. The negative pressure also draws or sucks latex disc 38 inward towards the interior of rigid container 10 so that latex disc 38 acts as a suction indicating means.

In use by the patient, the closed wound suction device is designed to be worn around the waist by means of a belt or the like which passes through flanges 12. The bow shape of the device makes it more comfortable to wear. This device is also designed so that the patient cannot tamper with it while the patient is wearing it. Therefore, after rigid wall 28 is locked in its extended position, pull tab 30 is removed by turning it approximately 90° and withdrawing key 56 from keyway 58 in rigid wall 28. This leaves only a rigid walled container so that the patient has nothing with which to tamper which could vary the negative pressure inside of rigid container 10.

After some fluid is collected, some or all of it is removed through aspiration port means 22. To accomplish this, cap 24 is removed and the device is tilted so that the fluid collects in the corner near aspiration port 44. The tip of a syringe is then inserted through puncturable flap 46 to draw off some of the fluid. It should be noted that as the fluid is drawn off, the negative pressure inside of rigid container 10 is increased. Therefore if fluid accumulates to such a degree that the negative pressure inside rigid container 10 is appreciably decreased, the negative pressure can be restored by simply removing the fluid in this manner. Likewise, if it is desired to increase the negative pressure inside of rigid container 10, air can also be removed as well. After the fluid has been withdrawn, cap 24 is replaced in case puncturable flap 46 develops a small leak. It should also be noted that the fluid cannot flow backwards from the inside of the rigid container 10 to the wound because of check valves 36. If for some reason, such as the inrush of air occurring when the airtight seal is suddenly lost, the fluid is urged back into drainage tubes 18, check valves 36 close so as to prevent this. After the portable wound suction device has served its purpose, it must be disposed of because it cannot be reused as rigid wall 28 is locked in place and cannot be readily removed from its operative position.

Figure 5:
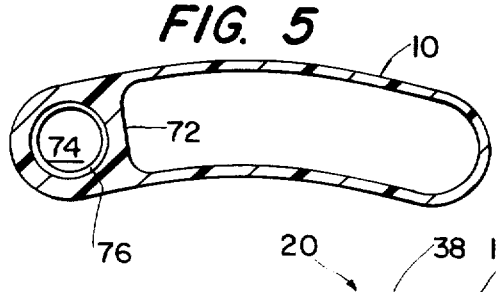
FIG. 5 is a cross-sectional view taken along the line 5—5 in FIG. 4.
Figure 6:
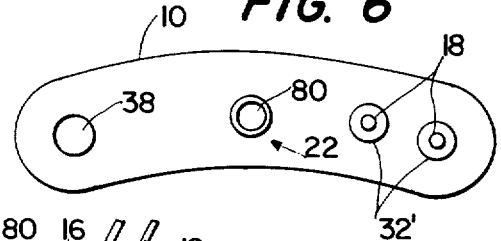
FIG. 6 is a top view of the embodiment depicted in FIG. 4.
Figure 4:
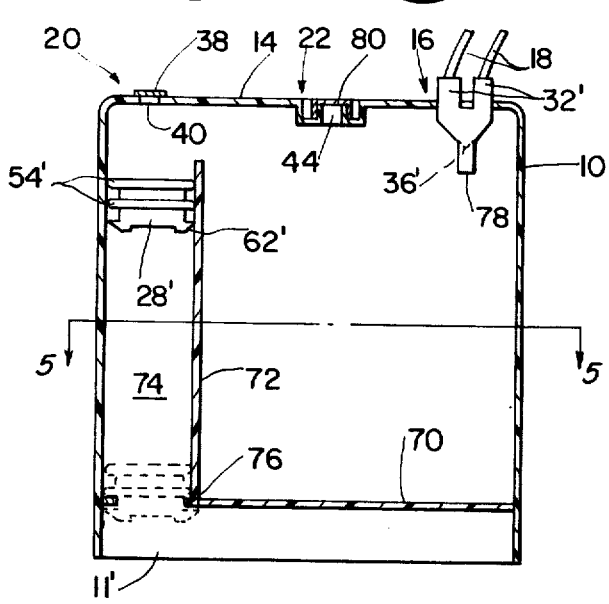
FIG. 4 is a cross-sectional view of another embodiment of the present invention with a rigid bottom wall and a movable rigid wall plug.

A further embodiment of the present invention is depicted in FIGS. 4, 5, and 6. This embodiment is used when a smaller negative pressure inside of rigid container 10 is desired. In this embodiment, a bottom wall 70 closes part of rigid container 10. Thus, open end 11' of rigid container 10 is only a small circular portion of the total area of the bottom of the container. Upstanding from bottom wall 70 is an interior wall 72 which forms a cylindrical chamber 74 with a raised lip 76. Rigid wall 28' is a cylindrical plug with annular gaskets 54' surrounding rigid wall 28' so that rigid wall 28' forms an airtight fit inside of cylindrical chamber 74. Like the previously described embodiment, rigid wall 28' is engaged by a detachable pull tab (not shown). Rigid wall 28' also has shoulder portions 62' which are resiliently urged outward.

As detailed in the previously described embodiments, this embodiment also has a suction indicating means 20 comprising a latex disc 38 and an opening 40. Similarly, drainage tubes 18 are attached to rubber nipples 32 which have a common outlet 78 and check valve 36' in this embodiment. Also in this embodiment, aspiration port means 22 is recessed inside of rigid container 10 so that a puncturable cap 80 is flush with the top of top wall 14 when it covers aspiration port 44.

In operation, this embodiment functions in the same manner as the previously described embodiment. Thus, with drainage tubes 18 suitably attached to the patient and to rubber nipples 32', rigid wall 28' is moved from a retracted inoperative position to an extended operative position by a detachable pull tab. In the retracted position, shoulder portions 62' of rigid wall 28' are pulled over and then locked under lip 76. Because rigid wall 28' and cylindrical chamber 74 represent only a small portion of the inside of rigid container 10, only a small negative pressure is created when rigid wall 28' is moved from its inoperative to operative position. This small pressure is still enough to pull latex disc 38 into opening 40 so that suction is indicated. Only a puncturable cap 80 need cover aspiration port 44, as puncturable cap 80 does not leak under the influence of such a small negative pressure even after the needle of a syringe has been passed through puncturable cap 80 to withdraw a sample of the fluid in rigid container 10.

Figure 8:
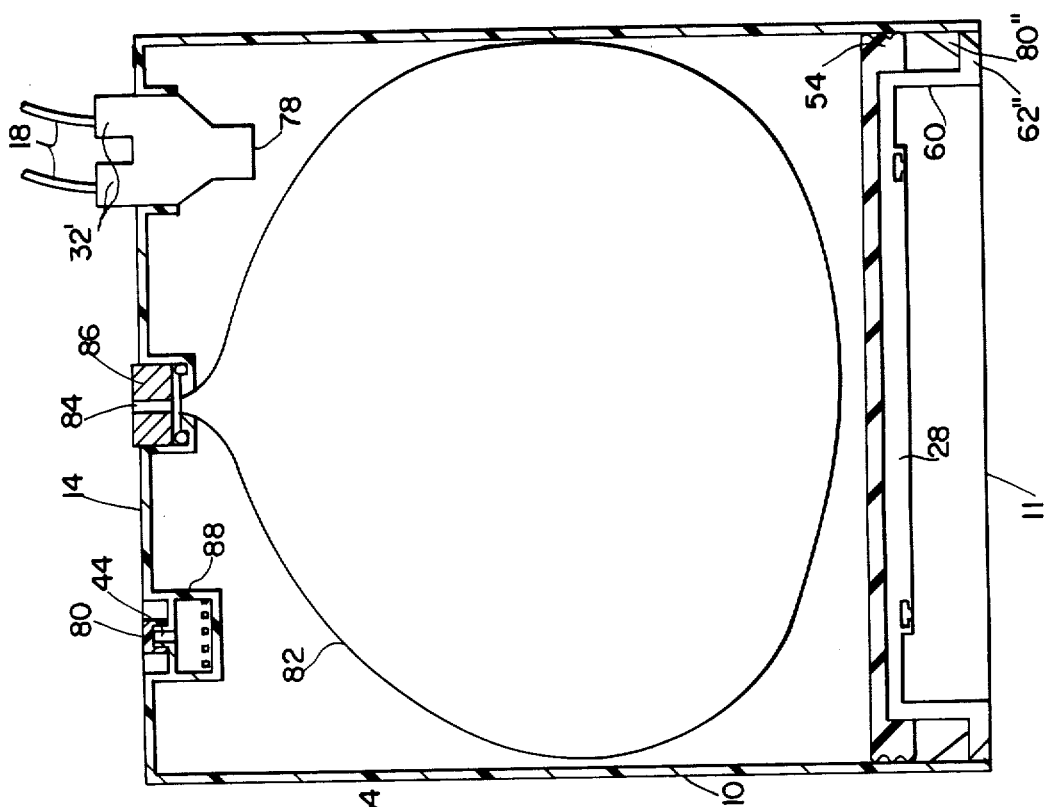
FIG. 8 is a cross-sectional view of the embodiment depicted in FIG. 7 with the movable wall in an extended position and with an inflated balloon inside the container.
Figure 7:
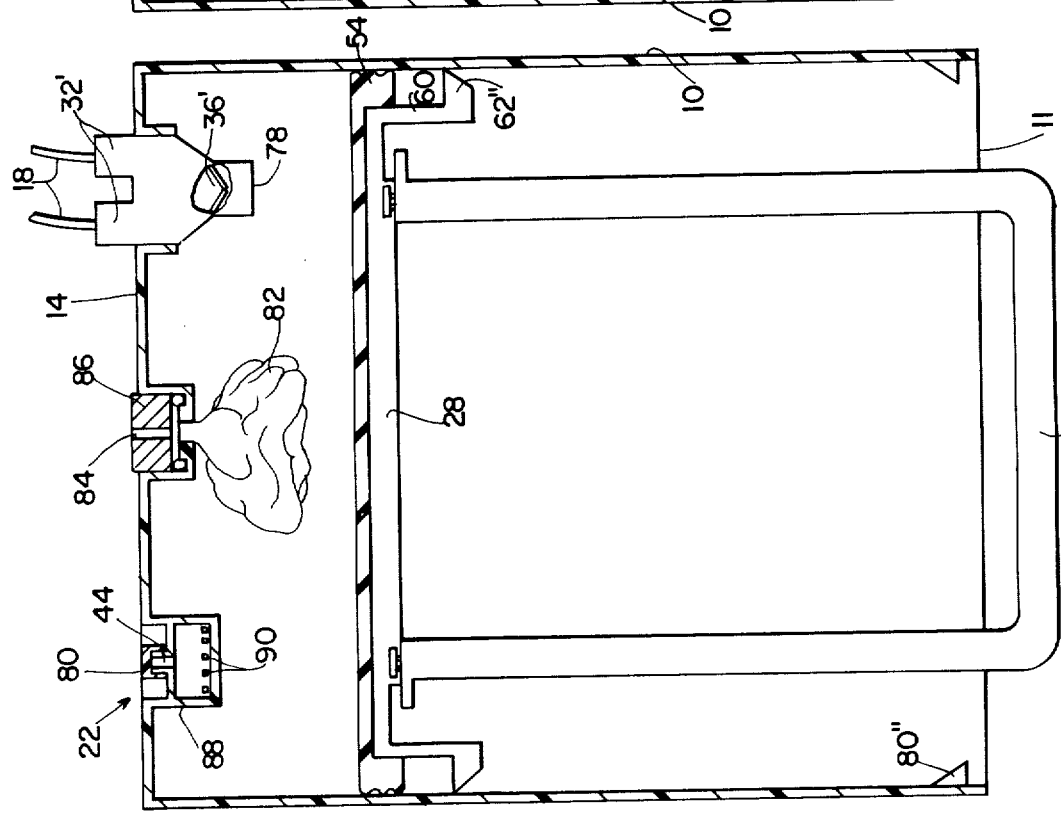
FIG. 7 is a cross-sectional view of still another embodiment of the present invention with a deflated balloon located inside of the rigid container.

Still another embodiment of a portable wound suction device which produces a smaller negative pressure in rigid container 10 is depicted in FIGS. 7 and 8. Like the first described embodiment, this embodiment has a rigid wall 28, which is the same size as top wall 14, with an annular gasket 54. In the same manner, rigid wall 28 is drawn from an inoperative to an operative position by a detachable pull tab 30''. Rigid wall 28 is likewise locked in an operative position by outwardly urged shoulder portions 62'' on arms 60 which engage lip 80''. This embodiment also has two rubber nipples 32, with a common outlet 78 and check valve 36', which receive drainage tubes 18.

Located inside of rigid container 10 is an inflatable lubricated balloon 82. The open end of inflatable balloon 82 is mounted on a recessed portion of top wall 14 by a suitable sealing plug 86 so that a vent 84 provides fluid communication between the interior of balloon 82 and the surrounding atmosphere. In order to protect inflatable balloon 82 from the sharp needle of a syringe which is passed through puncturable cap 80 and aspiration port 44, a cup-shaped enclosure 88 is located below aspiration port 44. Cup-shaped enclosure 88 has a solid bottom wall and openings 90 in the side walls.

In operation, this embodiment functions in a similar manner to the previously described embodiment. After drainage tubes 18 are connected to the patient and to the device, rigid wall 28 is pulled down and locked to its operative position by detachable handle 30''. As this is occurring, air is drawn into inflatable balloon 82 through vent 84. Inflatable balloon 82, depending on its resiliency, inflates and fills a portion of the interior of rigid container 10. The negative pressure which is created inside of rigid container 10 between the walls of rigid container 10 and the inflatable balloon 82 will vary according to the volume to which inflatable balloon 82 is inflated. The resiliency of inflatable balloon 82 determines the volume to which it inflates. Therefore, if inflatable balloon 82 is very resilient, it will inflate to almost the entire volume of rigid container 10 and only a small negative pressure is created. Conversely, if inflatable balloon 82 is relatively non-resilient, it will inflate only slightly creating a larger negative pressure. By varying the resiliency of inflatable balloon 82, a variety of portable wound suction devices can be made available to provide for a choice of the negative pressures created. As fluid collects in rigid container 10, the negative pressure tends to remain the same as balloon 82 is resiliently urged back to its uninflated position.

In order to obtain a sample of the fluid contained in rigid container 10, rigid container 10 is tilted until the fluid is located in the corner near the aspiration port 44. The fluid flows into cup-shaped enclosure 88 through openings 90. When the needle of a syringe is passed through puncturable cap 80 and aspiration port 44, the needle cannot pass beyond the bottom wall of cup-shaped enclosure 88. Thus, inflatable balloon 82 is protected from the needle, but the needle can still draw the fluid which readily flows into cup-shaped enclosure 88.

Other alternative embodiments of the present invention should be apparent to those of ordinary skill in the art. For instance, flanges 12 can be provided on an element which snaps onto rigid container 10. Additional flanges may be provided on the handle 30 in the FIG. 7 embodiment to insure uniform movement of wall 28. A self-adhesive backing may be applied to the container so that the closed wound suction device can be applied directly to the body of the patient. Also, to create a small negative pressure inside of rigid container 10, rigid wall 28 can be moved some distance toward open end 11 before rigid container 10 is made airtight. After rigid container 10 is made airtight, rigid wall 28 travels a smaller distance to its locked position and thus creates a smaller negative pressure.

Although the present invention has been described in detail with respect to exemplary embodiments thereof, it will be understood by those of ordinary skill in the art that variations and modifications may be effected within the scope and spirit of the invention.

I claim:

1. A closed wound suction device for collection of fluids from the area of tissue behind a closed wound comprising:
- a rigid container having an end wall and a peripheral side wall connected thereto, said rigid container having an opening in at least a portion of the end opposite the end wall between the peripheral enclosing side wall;
- movable piston closure means including a rigid wall for the opening of said container, said closure means being slidably movable in said container from a position in the interior of said container in a direction away from the end wall towards the opening;
- sealing means for providing an air tight seal between said closure means and said rigid container;
- a resilient lubricated balloon means located inside of said rigid container between said closure means and said closed end and normally occupying a small volume in an uninflated state, the interior of said balloon means being in fluid communication with the atmosphere;
- a variable volume pressure collection chamber for receiving the collected body fluids located between the outer surface of said balloon means and the interior surfaces of said container and said closure means;
- means for moving said closure means from a retracted, inoperative position within the interior of said container to an extended operative position adjacent the open end of said container whereby a negative pressure is created in said pressure collection chamber, the negative pressure in said pressure collection chamber being reduced as a result of the inflation of said balloon means in said pressure chamber such that a controlled vacuum is obtained in said pressure collection chamber;
- means to retain said closure means in the extended operative position; and
- port means in said rigid container in fluid communication with said pressure collection chamber and connectable in fluid communication with the closed wound whereby body fluids are drained from the closed wound to said pressure chamber, the negative pressure in said pressure chamber being maintained in said pressure chamber despite the introduction of fluid therein due to the shrinking volume of said balloon means as said balloon means is resiliently urged towards the uninflated position as the fluids enter said pressure chamber.

2. A closed wound suction device according to claim 1 and further including an aspiration port with a puncturable seal through which a sample of the fluid inside said container can be easily removed.

3. A closed wound suction device as claimed in claim 1 wherein said means to retain includes a locking means comprising resilient elements on said movable closure means and recesses on said peripheral side wall of said container adapted to receive said resilient elements whereby said closure means is securely locked in place.

4. A closed wound suction device as claimed in claim 1 wherein said peripheral side wall includes a curved portion to conform to the body of a user.

5. A closed wound suction device as claimed in claim 1 or 3 wherein said means for moving said closure means includes a removable pull tab attached to said closure means.

* * * * *